(12) United States Patent
Guala

(10) Patent No.: US 9,950,152 B2
(45) Date of Patent: Apr. 24, 2018

(54) CONNECTOR FOR MEDICAL LINES

(71) Applicant: Industrie Borla S.p.A., Moncalieri (Turin) (IT)

(72) Inventor: Gianni Guala, Turin (IT)

(73) Assignee: INDUSTRIE BORLA S.p.A., Moncalieri (Turin) (IT)

(*) Notice: Subject to any disclaimer, the term of this patent is extended or adjusted under 35 U.S.C. 154(b) by 20 days.

(21) Appl. No.: 14/894,681

(22) PCT Filed: May 29, 2014

(86) PCT No.: PCT/IB2014/061817
§ 371 (c)(1),
(2) Date: Nov. 30, 2015

(87) PCT Pub. No.: WO2014/191956
PCT Pub. Date: Dec. 4, 2014

(65) Prior Publication Data
US 2016/0106967 A1    Apr. 21, 2016

(30) Foreign Application Priority Data

May 29, 2013 (IT) .............................. TO2013A0433

(51) Int. Cl.
*A61M 39/10* (2006.01)
*A61J 1/14* (2006.01)
*A61B 17/00* (2006.01)

(52) U.S. Cl.
CPC ........ *A61M 39/10* (2013.01); *A61M 39/1011* (2013.01); *A61B 2017/00477* (2013.01);
(Continued)

(58) Field of Classification Search
CPC .............. A61M 39/10; A61M 39/1011; A61M 2039/1016; A61M 2039/1033;
(Continued)

(56) References Cited

U.S. PATENT DOCUMENTS 4,432,759 A * 2/1984 Gross ................. A61M 39/1011
285/419
4,473,162 A * 9/1984 Donoghue ........... B65D 50/046
215/209

(Continued)

FOREIGN PATENT DOCUMENTS

DE    4318101 A1    12/1994
EP    0443868 A1    8/1991
(Continued)

OTHER PUBLICATIONS

English translation of WO 2012002316 A1.*

*Primary Examiner* — Nathan R Price
*Assistant Examiner* — Dung Ulsh
(74) *Attorney, Agent, or Firm* — Heslin Rothenberg Farley & Mesiti P.C.; Victor A. Cardona, Esq.

(57) ABSTRACT

A connector for medical lines includes a tubular body having a male luer-lock fitting at one end, intended to be screw-coupled with a complementary female fitting. An outer jacket is coupled in unidirectional rotation with the tubular body in the direction corresponding to the screwing of the male fitting and freely rotatable in the opposite direction. For selectively coupling the outer jacket with the tubular body in the direction corresponding to the unscrewing of the male fitting, at least one side push-button carried by said outer jacket is provided.

9 Claims, 3 Drawing Sheets

(52) U.S. Cl.
CPC ..... *A61J 1/1475* (2013.01); *A61M 2039/1016* (2013.01); *A61M 2039/1033* (2013.01)

(58) Field of Classification Search
CPC .......... A61B 2017/00477; A61J 1/1475; F16L 37/0847; F16L 37/091; F16L 37/096; F16L 37/098
See application file for complete search history.

(56) References Cited

U.S. PATENT DOCUMENTS

| | | | | |
|---|---|---|---|---|
| 5,197,895 | A * | 3/1993 | Stupecky | A61B 5/087 285/119 |
| 5,403,840 | A * | 4/1995 | Vikmon | C08B 37/0015 424/488 |
| 5,531,695 | A * | 7/1996 | Swisher | A61M 39/1011 285/45 |
| 5,702,374 | A * | 12/1997 | Johnson | A61M 39/10 128/912 |
| 6,036,036 | A * | 3/2000 | Bilani | B65D 50/046 215/216 |
| 6,217,564 | B1 | 4/2001 | Peters et al. | |
| 6,508,807 | B1 * | 1/2003 | Peters | A61M 39/1011 604/533 |
| 6,796,451 | B2 * | 9/2004 | Harris | F01P 11/0238 220/203.22 |
| 7,497,484 | B2 * | 3/2009 | Ziman | A61M 39/10 285/396 |
| 7,731,708 | B2 * | 6/2010 | Haarala | A61M 25/0097 604/533 |
| 7,784,766 | B2 * | 8/2010 | Guala | A61M 39/045 251/149.6 |
| 8,048,038 | B2 * | 11/2011 | Guala | A61M 39/045 251/149.6 |
| 8,308,010 | B2 * | 11/2012 | Letica | B65D 43/0279 215/216 |
| 2003/0201639 | A1 * | 10/2003 | Korkor | A61M 39/1011 285/81 |
| 2005/0029810 | A1 * | 2/2005 | Dong | F16L 37/098 285/308 |
| 2005/0225082 | A1 | 10/2005 | Dalle et al. | |
| 2006/0089594 | A1 * | 4/2006 | Landau | A61M 5/2033 604/68 |
| 2006/0161115 | A1 * | 7/2006 | Fangrow | A61M 39/26 604/249 |
| 2007/0060902 | A1 * | 3/2007 | Brandenburger | A61J 1/10 604/403 |
| 2007/0088327 | A1 * | 4/2007 | Guala | A61M 39/10 604/533 |
| 2007/0093109 | A1 * | 4/2007 | Czarnyszka | H01R 13/622 439/321 |
| 2007/0129705 | A1 * | 6/2007 | Trombley, III | A61M 39/10 604/523 |
| 2007/0129719 | A1 * | 6/2007 | Kendale | A61B 1/00096 606/41 |
| 2007/0218757 | A1 * | 9/2007 | Guala | A61M 39/045 439/589 |
| 2007/0249197 | A1 * | 10/2007 | Spranger | A61M 39/1011 439/152 |
| 2008/0129042 | A1 | 6/2008 | Weigel et al. | |
| 2008/0172039 | A1 * | 7/2008 | Raines | A61M 39/1011 604/533 |
| 2008/0190485 | A1 * | 8/2008 | Guala | A61M 39/045 137/1 |
| 2008/0287920 | A1 * | 11/2008 | Fangrow | A61M 39/1011 604/535 |
| 2009/0143758 | A1 * | 6/2009 | Okiyama | A61J 1/1475 604/408 |
| 2009/0287140 | A1 * | 11/2009 | Rittman, III | A61N 1/403 604/21 |
| 2009/0292274 | A1 * | 11/2009 | Guala | A61M 39/26 604/533 |
| 2010/0210990 | A1 * | 8/2010 | Lyons | A61M 39/1011 604/6.16 |
| 2010/0256573 | A1 * | 10/2010 | Mansour | A61M 39/1011 604/256 |
| 2011/0015580 | A1 * | 1/2011 | Stroup | A61M 5/16881 604/207 |
| 2011/0044850 | A1 * | 2/2011 | Solomon | A61M 39/162 422/28 |
| 2011/0106046 | A1 * | 5/2011 | Hiranuma | A61J 1/2096 604/414 |
| 2011/0152841 | A1 * | 6/2011 | Nemoto | A61M 39/26 604/533 |
| 2011/0196314 | A1 * | 8/2011 | Smutney | A61M 3/0279 604/247 |
| 2011/0224651 | A1 * | 9/2011 | Ziman | A61M 39/10 604/533 |
| 2012/0041426 | A1 * | 2/2012 | Bizup | A61M 39/1011 604/536 |
| 2012/0130337 | A1 * | 5/2012 | Guala | A61M 5/1408 604/414 |
| 2013/0072893 | A1 * | 3/2013 | Takemoto | A61J 1/2096 604/403 |
| 2013/0144246 | A1 * | 6/2013 | Takemoto | A61J 1/2096 604/403 |
| 2014/0246616 | A1 * | 9/2014 | Fangrow | A61M 39/26 251/148 |
| 2015/0209568 | A1 * | 7/2015 | Rosenquist | A61M 39/10 285/45 |

FOREIGN PATENT DOCUMENTS

| | | | | |
|---|---|---|---|---|
| GB | | 2379253 A | 3/2003 | |
| WO | WO 2012002316 A1 * | | 1/2012 | ............ A61J 1/2096 |

* cited by examiner

CONNECTOR FOR MEDICAL LINES

CROSS REFERENCE TO RELATED APPLICATIONS

This application is a national stage filing under section 371 of International Application No. PCT/IB2014/061817, filed on May 29, 2014, and published in English on Dec. 4, 2014, as WO 2014/191956 A1, and claims priority of Italian application No. TO2013A000433 filed on May 29, 2013, the entire disclosure of these applications being hereby incorporated herein by reference.

FIELD OF THE INVENTION

The present invention relates to connectors for medical lines of the type comprising a tubular body having a male luer-lock fitting at one end, including an inner tubular element and an innerly threaded outer hollow element intended to be screw-coupled with a complementary female fitting.

STATE OF THE PRIOR ART

In connectors of the type defined above, when the male fitting is coupled and screwed to the complementary female fitting, there is the risk that the two fittings can become unscrewed and separated from each other accidentally, or due to a wrong manoeuvre, which may lead to the loss of fluids, and consequently to possible critical risks for the patient to whom the medical line with the connector is connected, when in use.

One solution to this problem, proposed by the Applicant in the European patent application no. 13150798.1 (unpublished at the priority date of the present application), consists of providing the connector with an outer jacket, coupled in unidirectional rotation with the tubular body in the direction corresponding to the screwing of the male fitting relative to the complementary female fitting, and freely rotatable in the opposite direction corresponding to the unscrewing of the male fitting. In this solution, the tubular body and the outer jacket are mutually axially displaceable, against the action of elastic contrast means, from the position in which they are rotationally coupled together in the screwing direction of the male fitting, to a position in which the torsional mutual coupling means rotationally couple the jacket and the tubular body in the direction corresponding to the unscrewing of the male fitting.

As far as this solution is entirely suitable for effectively solving the problem mentioned above, the intervention of these torsional coupling means, which requires mutual axial displacement between the outer jacket and the tubular body, can result in being unintuitive for the operator and sometimes inconvenient or difficult.

SUMMARY OF THE INVENTION

The present invention aims to resolve the aforesaid technical problem, and particularly aims to render the operation of the aforesaid torsional coupling means more immediate and straightforward, said means allowing the unscrewing of the male fitting of the connector ensuring, at the same time, a high degree of safety against the effects of the risk of erroneous or accidental unscrewing.

According to the invention, this object is achieved thanks to a connector as defined in claim 1.

Thanks to this solution idea, the voluntary operation that allows the unscrewing of the connector does not require any mutual axial translation between the outer jacket and the tubular body of the connector, but is produced in a more simple, intuitive and immediate manner through the operation of the side push-button.

The side push-button is conveniently provided with an engagement tooth, and the tubular body is externally provided with at least one striker tooth. The side push-button is essentially radially displaceable with respect to the outer jacket between a stable, inoperative position and an unstable operative position in which the engagement tooth interacts with the striker tooth.

The push-button advantageously consists of an elastically deformable element, integrally formed with the outer jacket, and bearing the said engagement tooth at its free end.

To additionally render this manoeuvre even more convenient and straightforward, the connector according to the invention conveniently comprises a pair of diametrically opposite side push-buttons, which cooperate with a pair of diametrically opposite respective striker teeth of the tubular body.

The connector according to the invention can be advantageously used in multiple applications, such as for a needle point: in this case, a resilient body, adapted to be pierced by a needle or passed-through by a cannula, is fitted at the end of the tubular body, opposite to said male fitting.

BRIEF DESCRIPTION OF THE DRAWINGS

The invention will now be described in detail with reference to the accompanying drawings, provided purely by way of non-limiting example, in which.

DETAILED DESCRIPTION OF THE INVENTION

Figure 1:
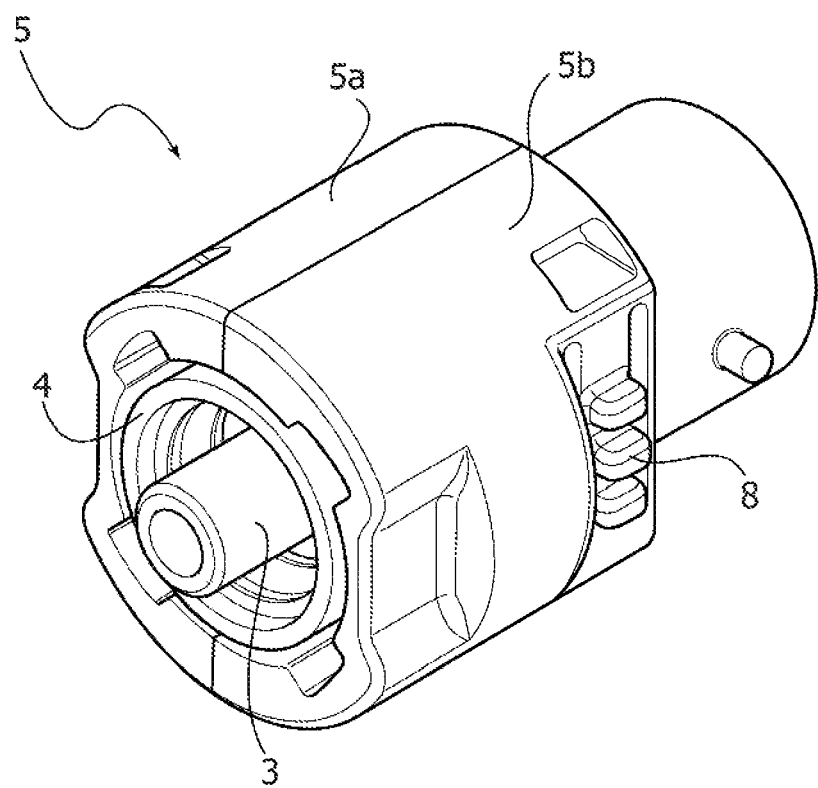
FIG. 1 is a schematic perspective view of a connector for medical lines, which forms an embodiment of the invention.
Figure 2:
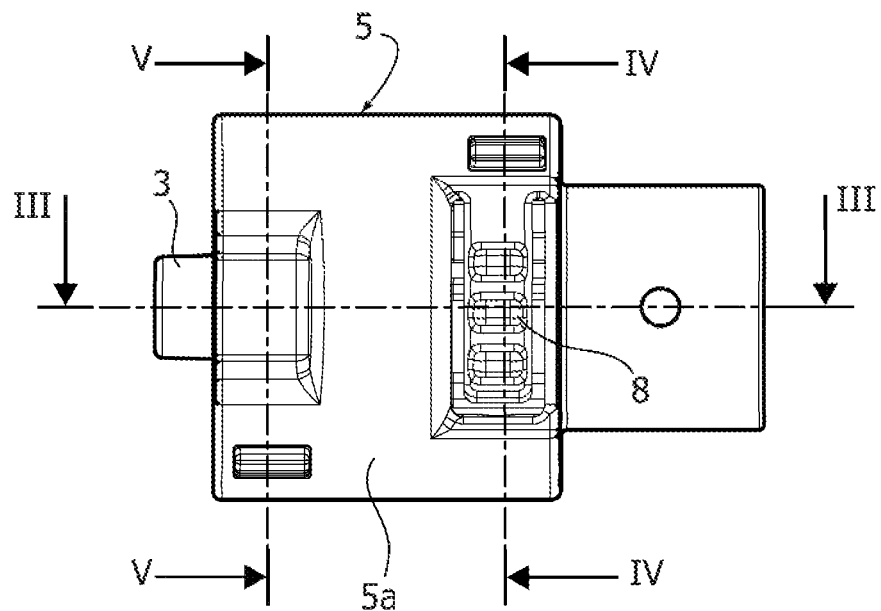
FIG. 2 is a side elevational view of the connector.
Figure 3:
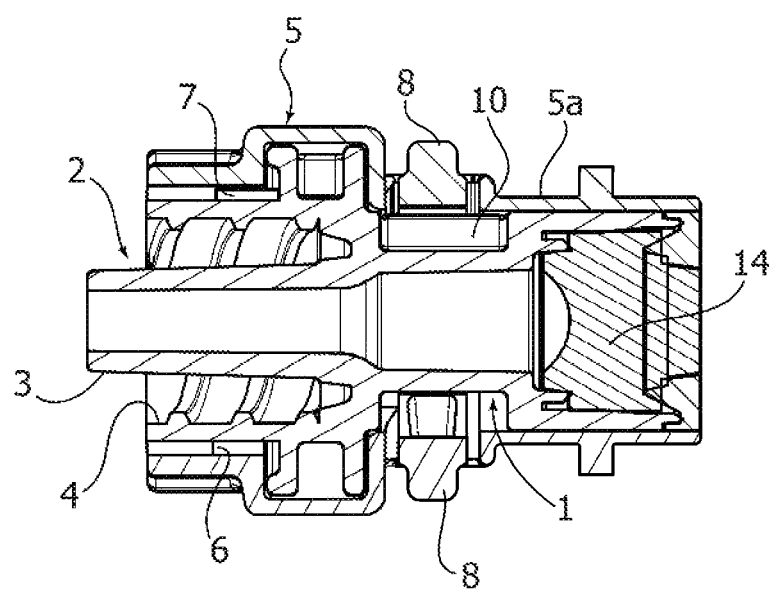
FIG. 3 is an axial section view along the line of FIG. 2.

The connector for medical lines represented in the example relates to a needle point ("injection site"): however, the invention is applicable to a multiplicity of connectors of different types having diverse functions.

Referring to the drawings, the connector comprises a tubular body 1 formed with a male luer-lock fitting 2 at one end, including an inner tubular element 3 with a slightly conical outer surface, and an innerly threaded hollow element 4 intended to be screw-coupled with a complementary female luer-lock fitting.

Numeral 5 indicates an outer jacket that coaxially covers the tubular body 2 for almost its entire length and is coupled thereto in unidirectional rotation in the direction corresponding to the screwing of the male luer-lock fitting 2, while normally it is freely rotatable in the opposite direction, corresponding to the unscrewing.

For rotational coupling in the screwing direction, the outer jacket 5 is internally provided with a crown of ratchet teeth 6, integrally formed by moulding, and elastically springing, cooperating with a crown of engagement teeth 7 formed on the outer surface of the outer hollow element of the male fitting 2. In the screwing direction, the ratchet teeth 6 engage with the engagement teeth 7 so that the outer jacket 5 rotates the tubular body 1, while in the opposite direction, the ratchet teeth 6 elastically jump above the engagement teeth 7, so that the rotation of the outer jacket 5 does not produce any rotation of the tubular body 1. This avoids accidental or erroneous unscrewing of the male luer-lock fitting 2, during use, from the complementary female connector fitting to which the connector is coupled.

To allow, however, the voluntary unscrewing of the connector, the invention provides a manually operable torsional coupling system, in order to also couple the outer jacket 5 with the tubular body 1 in the direction corresponding to the unscrewing of the male luer-lock fitting 2.

This coupling system comprises at least one side push-button, and preferably two diametrically opposite side push-buttons, indicated with 8, integrally formed with the outer jacket 5 at its respective windows. Each push-button 8 has an engagement tooth 9 at its free end, and is essentially radially displaceable with respect to the jacket 5, between a stable inoperative position (represented in FIG. 4) and an unstable operative position in which the respective end tooth 9 engages a corresponding striker tooth 10 formed outside the tubular body 1, at the rear of the male luer-lock fitting 2. The displacement from the inoperative position to the operative one requires a manually-applied pressure to the two side push-buttons 8, the release of which produces the elastic return to the inoperative position.

Figure 4:
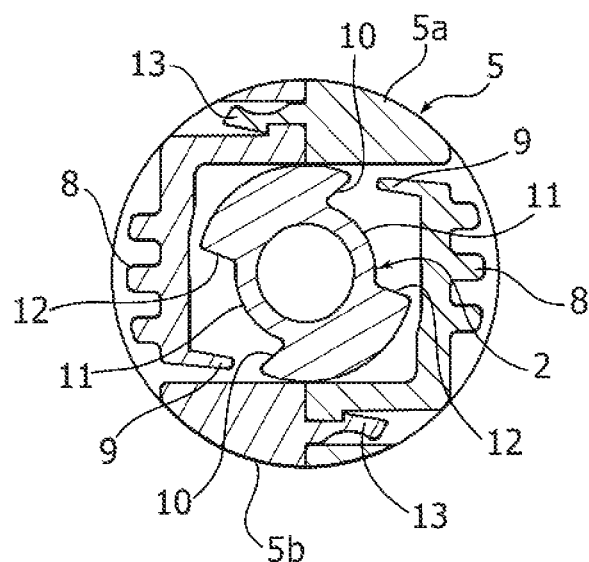
FIG. 4 is a cross sectional view along the line IV-IV of FIG. 2.
Figure 5:
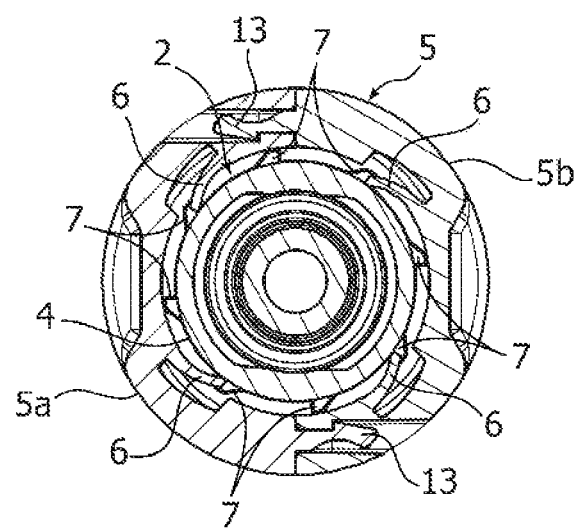
FIG. 5 is a cross sectional view along the line V-V of FIG. 2.

As is evident in FIG. 4, the striker teeth 10 are formed from end walls at an acute angle with a pair of contrasting recesses 11 of the tubular body 1, the opposite ends 12 of which are at an obtuse angle.

The outer jacket 5, with the ratchet teeth 6 and the push-buttons 8 and the relative engagement teeth 9, is conveniently formed by two identical half-shells 5a, 5b, coupled to each other on the tubular body 1, and joined by their respective irreversible snap-fit coupling means 13.

As already revealed, the connector described here by way of non-limiting example, is configured to form a needle point: to this effect, a resilient body 14, adapted to be pierced by a needle or passed-through by a cannula, is inserted and axially locked within the ends of the tubular body 1 opposite to the male luer-lock fitting 2.

Of course, the details of construction and the embodiments may vary widely with respect to those described and illustrated, without departing from the scope of the present invention as defined in the following claims.

The invention claimed is:

1. A connector for medical lines, comprising;
    a tubular body having a male luer-lock fitting at one end, including an inner tubular element and an innerly threaded outer hollow element intended to be screw-coupled with a complementary female fitting;
    an outer jacket coupled in an unidirectional rotation with the tubular body in a direction corresponding to a screwing of said male luer-lock fitting and freely rotatable in an opposite direction of unscrewing; and
    at least one side push-button carried by said outer jacket and radially displaceable relative to said outer jacket to selectively couple said outer jacket with the tubular body in a direction corresponding to an unscrewing of said male luer-lock fitting;
    said innerly threaded outer hollow element of the male luer-lock fitting provided radially externally with a crown of engagement teeth co-operating with a crown of springing ratchet teeth provided radially internally of said outer jacket for a mutual unidirectional rotational coupling in the direction corresponding to the screwing of said male luer-lock fitting;
    said crown of springing ratchet teeth elastically springing such that each springing ratchet tooth of said crown of springing ratchet teeth elastically jumps over an engagement tooth of said crown of engagement teeth during the rotation in the direction of the unscrewing to avoid accidental unscrewing of the male luer-lock fitting during use; and
    wherein a resilient body, adapted to be pierced by a needle or passed-through by a cannula, is inserted into the end of said tubular body opposite to said male luer-lock fitting.

2. A connector according to claim 1, wherein said at least one side push-button is provided with an engagement tooth and said tubular body is provided externally with at least one striker tooth, said side push-button essentially being radially displaceable between a stable inoperative position and an unstable operative position wherein said engagement tooth interacts with said striker tooth.

3. A connector according to claim 2, wherein said at least one side push-button consists of an elastically deformable element integrally formed with the outer jacket and bearing said engagement tooth at its free end.

4. A connector according to claim 1, further comprising a pair of side push-buttons, diametrically opposite to each other.

5. A connector according to claim 1, wherein said outer jacket is formed by two half-shells mutually joined on said tubular body.

6. A connector according to claim 5, wherein said two half-shells are mutually joined by a snap-fit coupling.

7. A connector for medical lines, comprising;
    a tubular body having a male luer-lock fitting at one end, including an inner tubular element and an innerly threaded outer hollow element intended to be screw-coupled with a complementary female fitting;
    an outer jacket coupled in unidirectional rotation with the tubular body in a direction corresponding to a screwing of said male luer-lock fitting and freely rotatable in an opposite direction;
    at least one side push-button carried by said outer jacket and radially displaceable relative to said outer jacket to selectively couple said outer jacket with the tubular body in a direction corresponding to an unscrewing of said male luer-lock fitting;
    said male luer-lock fitting comprising a first striker tooth configured to engage said at least one side push-button to selectively couple said outer jacket with the tubular body, said first striker tooth located at a rear end of said male luer-lock fitting and on an external surface of said tubular body, said first striker tooth separated by a recess of said tubular body from an opposite end of a recess surface bounding said recess formed at an obtuse angle relative to said recess surface, and said first striker tooth formed at an acute angle relative to said recess surface;
    said innerly threaded outer hollow element of the male luer-lock fitting provided radially externally with a crown of engagement teeth co-operating with a crown of springing ratchet teeth provided radially internally of said outer jacket for a mutual unidirectional rotational coupling in the direction corresponding to the screwing of said male luer-lock fitting; and
    said crown of springing ratchet teeth elastically springing such that each springing ratchet tooth of said crown of springing ratchet teeth elastically jumps over an engagement tooth of said crown of engagement teeth during the rotation in the direction of the unscrewing to avoid accidental unscrewing of the male luer-lock fitting during use.

8. The connector of claim 7 further comprising a second striker tooth located at said rear end said male luer-lock fitting and on said external surface of said tubular body, said second striker tooth separated by a second recess of said tubular body from a second opposite end of a second recess surface bounding said second recess formed at a second obtuse angle relative to said second recess surface, and said second striker tooth formed at an acute angle relative to said second recess surface.

9. The connector of claim 8 wherein said first recess and said second recess are located on opposite sides of said tubular body.

* * * * *